United States Patent [19]

Smith et al.

[11] Patent Number: 5,127,997
[45] Date of Patent: Jul. 7, 1992

[54] PURIFICATION OF PROPYLENE OXIDE BY LIQUID EXTRACTION

[75] Inventors: William A. Smith, Austin, Tex.;
Robert A. Meyer, Ballwin, Mo.;
Eileen T. Nguyen, Houston, Tex.

[73] Assignee: Texaco Chemical Company, White Plains, N.Y.

[21] Appl. No.: 697,385

[22] Filed: May 9, 1991

[51] Int. Cl.⁵ .................... B01D 3/34; C07D 301/32
[52] U.S. Cl. ........................ 203/45; 203/81; 549/541
[58] Field of Search ............. 203/43, 45, 71, 81, 203/74; 549/541

[56] References Cited

U.S. PATENT DOCUMENTS

| | | | |
|---|---|---|---|
| 3,039,940 | 6/1962 | Prinz et al. | 549/541 |
| 3,338,800 | 8/1967 | Binning et al. | 549/541 |
| 3,464,897 | 9/1969 | Jubin | 549/541 |
| 3,520,907 | 7/1970 | Taylor et al. | 549/541 |
| 3,607,669 | 9/1971 | Jubin | 549/541 |
| 3,843,488 | 10/1974 | Schmidt et al. | 549/541 |
| 3,881,996 | 5/1975 | Schmidt | 549/541 |
| 3,909,366 | 9/1975 | Schmidt et al. | 549/541 |
| 4,014,753 | 3/1977 | Fuchs et al. | 549/541 |
| 4,113,747 | 9/1978 | Prescher et al. | 549/541 |
| 4,971,661 | 11/1990 | Meyer et al. | 203/54 |
| 4,977,285 | 12/1990 | Marquis et al. | 549/541 |
| 5,006,206 | 4/1991 | Shih et al. | 549/541 |

FOREIGN PATENT DOCUMENTS

959218 5/1964 United Kingdom ............... 549/541

Primary Examiner—Wilbur Bascomb, Jr.
Attorney, Agent, or Firm—Jack H. Park; Kenneth R. Priem; Carl G. Ries

[57] ABSTRACT

Purified propylene oxide is recovered from an impure propylene oxide feedstock contaminated with more than 50 ppm of six carbon atom hydrocarbon impurities by a solvent extraction process wherein:

an impure propylene oxide feedstock is charged to a liquid/liquid extraction zone and contacted therein with an extractant consisting essentially of water and a paraffinic hydrocarbon containing 8 to 10 carbon atoms, and resolved therein into a raffinate consisting essentially of an aqueous solution of propylene oxide and into an extract comprising the paraffinic hydrocarbon and the 6 carbon atom impurities initially present in the propylene oxide feedstock.

4 Claims, 2 Drawing Sheets

PURIFICATION OF PROPYLENE OXIDE BY LIQUID EXTRACTION

BACKGROUND OF THE INVENTION

1. Technical Field of the Invention

This invention relates to the purification of propylene oxide. More particularly, this invention relates to a method for the purification of propylene oxide formed by the reaction of a hydroperoxide such as tertiary butyl hydroperoxide with propylene.

In the epoxidation of propylene to form propylene oxide by the molybdenum catalyzed reaction of a hydroperoxide such as tertiary butyl hydroperoxide with propylene, a variety of side products accumulate in the reaction mixture. The reaction side products include oxygenated materials such as methyl formate, acetone, isobutyraldehyde, methanol, isopropyl alcohol, etc. Another group of side products that accumulate in comparatively small amounts, such as amounts within the range of about 0.01 to about 0.1 wt. % (i.e., about 100 to 1,000 ppm), based on propylene oxide, are 6 carbon atom hydrocarbon oligomers or dimers of propylene such as 2-methyl pentane, 4-methyl-1-pentene, etc. However, it is normally desirable to provide a propylene oxide product containing about 0.005 wt. % or less of the propylene dimer impurities. The hydrocarbon dimer impurities have boiling point characteristics similar to the boiling properties of propylene oxide and, therefore, they are removed only with great difficulty.

It has been discovered in accordance with the present invention that a purified propylene oxide product having a propylene dimer content of about 0.005 wt. % or less (e.g., from about 1 to about 50 parts per million) can be obtained by liquid-liquid extraction of an impure propylene oxide feedstock with a co-solvent extractant mixture of a $C_8$–$C_{10}$ paraffinic hydrocarbon and water.

2. Prior Art

The coproduction of an epoxide such as propylene oxide together with a coproduct such as tertiary butyl alcohol by the reaction of an olefin with a hydroperoxide is disclosed in Kollar U.S. Pat. Nos. 3,350,422 and 3,351,635 which are directed to the catalytic epoxidation of an olefin by reaction with a hydroperoxide such as tertiary butyl hydroperoxide. When the olefin is propylene and the hydroperoxide is tertiary butyl hydroperoxide, the principle reaction products are propylene oxide and tertiary butyl alcohol.

Suitable molybdenum catalysts and method of preparing propylene oxides from tertiary butyl peroxide using the catalyst are disclosed, for example, in Marquis et al. U.S. Pat. No. 4,626,596, Marquis et al. U.S. Pat. No. 4,650,886, Marquis et al. U.S. Pat. No. 4,654,427, Marquis et al. U.S. Pat. No. 4,703,027, and Marquis et al. U.S. Pat. No. 4,845,251.

Among the U.S. patents that have issued directed to olefin epoxidation may be mentioned, for example, Marquis et al. U.S. Pat. No. 4,891,437 wherein a process is disclosed wherein tertiary butyl hydroperoxide is reacted with propylene in the presence of a molybdenum catalyst in a polar medium. Other patents directed to olefin epoxidation include patents such as Sargenti U.S. Pat. No. 3,666,777, Stein et al. U.S. Pat. No. 3,849,451, Russell U.S. Pat. No. 3,418,430, Scheng et al. U.S. Pat. No. 3,434,975, etc.

U.S. Pat. No. 3,909,366 teaches that propylene oxide may be purified with respect to contaminating paraffinic and olefinic hydrocarbons by extractive distillation in the presence of an aromatic hydrocarbon containing from 6 to 12 carbon atoms.

Jubin U.S. Pat. No. 3,464,897 is directed to a method for the separation of contaminating paraffinic and olefinic hydrocarbons such as propylene dimers by azeotropic distillation in the presence of an open chain or cyclic paraffin containing from 8 to 12 carbon atoms. In this regard, see also U.S. Pat. No. 3,607,669.

Schmidt et al. U.S. Pat. No. 3,843,488 also discloses a method for the removal of hexenes, hexanes, methyl pentenes and methyl pentanes from propylene oxide by azeotropic distillation in the presence of an alkane, an alkene or a naphthene containing from 8 to 15 carbon atoms.

Kageyama et al. U.S. Pat. No. 3,838,020 discloses a method for the extractive distillation of propylene oxide in order to remove impurities using an extractive solvent mixture composed of a mixture of a glycol and dioxane, butyl acetate, 2-ethyl hexanol or mixtures thereof.

SUMMARY OF THE INVENTION

In accordance with the present invention, a purified propylene oxide product fraction is obtained containing, suitably, from about 1 to about 50 ppm of 6 carbon atom hydrocarbon impurities including hexanes, hexenes, methyl pentenes and methyl pentanes by liquid-liquid countercurrent extraction of an impure propylene oxide feedstock contaminated with more than about 50 ppm of $C_6$ hydrocarbon impurities with an extractant consisting essentially of water and a paraffinic hydrocarbon containing 8 to 10 carbon atoms.

Propylene oxide is soluble in paraffins such as propylene dimers (hexanes, hexenes, methyl pentanes and methyl pentenes) and $C_8$–$C_{10}$ paraffins and, therefore, extractive distillation, rather than solvent extraction, has been favored as means of separating propylene dimer impurities from propylene oxide. In accordance with the present invention, however, a $C_8$–$C_{10}$ paraffin and water, as a co-solvent, are used to sucessfully extract trace quantities of $C_6$ hydrocarbon impurities, such as propylene dimers from propylene oxide.

In a preferred embodiment, this invention is directed to a process wherein a reaction product formed by the epoxidation of propylene with tertiary butyl hydroperoxide in the presence of a molybdenum catalyst to provide a reaction mixture comprising unreacted propylene, unreacted tertiary butyl hydroperoxide, tertiary butyl alcohol, propylene oxide, and impurities including oxygenated impurities and $C_6$ hydrocarbon impurities is separated by distillation in a product separation zone into a plurality of distillation fractions including a light impurities fraction, a propylene fraction, a tertiary butyl alcohol fraction, and an impure propylene oxide feedstock fraction and wherein the impure propylene oxide feedstock fraction, which is contaminated with more than about 50 ppm of $C_6$ hydrocarbon impurities is subjected to solvent extraction in a solvent extraction zone in the presence of an extractant consisting essentially of water and a paraffinic hydrocarbon containing 8 to 10 carbon atoms to provide a raffinate composed of a mixture of water and propylene oxide that is substantially free from the $C_6$ hydrocarbon contaminants and which may be resolved by simple distillation into a water fraction and a propylene oxide product fraction containing less than 50 ppm of $C_6$ hydrocarbon impurities.

Preferably, water and the $C_8$-$C_{10}$ paraffin will be used in amounts such that the volume ratio of water to propylene oxide is in the range of about 1 to about 5 unit volumes of water per unit volume of propylene oxide and such that the volume ratio of $C_8$-$C_{10}$ paraffin to propylene oxide is in the range of about 0.5 to about 5 unit volumes of $C_8$-$C_{10}$ paraffin per unit volume of propylene oxide.

DESCRIPTION OF THE PREFERRED EMBODIMENT

Figure 1:
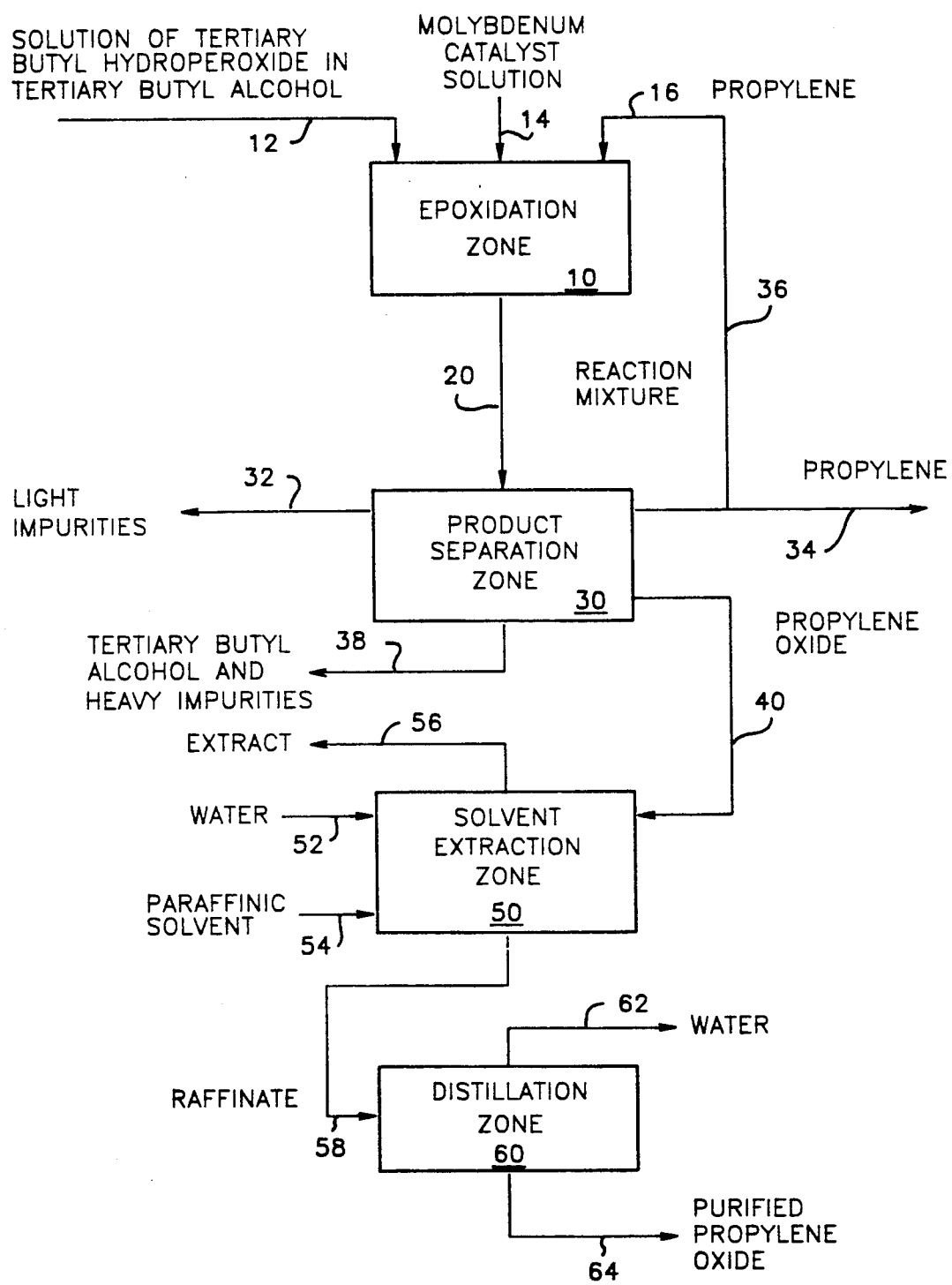
FIG. 1 is a schematic block diagram illustrating a preferred embodiment of the invention.

Turning now to the drawings, there is shown in FIG. 1 a schematic block diagram illustrating a preferred method of practicing the process of the present invention. In the drawing, conventional parts such as valves, pumps, temperature sensors, pressure sensors, heaters, coolers, control and flow regulation apparatus, reboilers, reflux condensers, etc., have been omitted.

In accordance with the present invention, an epoxidation zone 10 is provided such as an epoxidation zone of the type described, for example, in Marquis et al. U.S. Pat. No. 4,891,437, such epoxidation zone being designated generally by the numeral 10.

In the manner disclosed, for example, in Marquis et al. U.S. Pat. No. 4,891,437, a solution of tertiary butyl hydroperoxide in tertiary butyl alcohol is charged to the epoxidation reaction zone 10 by a charge line 12 together with a molybdenum catalyst solution charged by a line 14 and a propylene feedstock charge by a line 16.

Within the epoxidation zone 10 a molybdenum catalyzed reaction occurs between the tertiary butyl hydroperoxide and the propylene resulting in the formation of a reaction mixture comprising unreacted propylene, unreacted tertiary butyl hydroperoxide, tertiary butyl alcohol, propylene oxide and impurities including both oxygen-containing impurities and $C_6$ hydrocarbon impurities.

The oxygenated impurities will typically include compounds such as methyl formate, acetone, isobutyraldehyde, methanol, isopropyl alcohol, etc.

The $C_6$ hydrocarbon impurities will normally comprise hexanes, hexenes, methyl pentenes and methyl pentanes such as hexane, hexene, 2-methyl pentane, 4-methyl pentene-1, 4-methyl pentene-2, 2-methyl pentene-1, 2-methyl pentene-2, etc.

The thus formed reaction mixture is discharged from the epoxidation zone 10 by a discharge line 20 leading to a product separation zone 30 which will suitably comprise a plurality of distillation columns operated, for example, in the manner shown in Sanderson et al. U.S. Pat. No. 4,810,809 where the reaction product 20 is resolved into a plurality of distillation fractions. Typically, the distillation fractions will include a light impurities fraction 32 composed of oxygenated impurities having boiling points above the boiling point of tertiary butyl alcohol, a propylene fraction 34 which may suitably be recycled to the epoxidation zone 10 by way of a recycle line 36 leading to propylene charge line 16, a tertiary butyl alcohol distillation fraction 38 which will normally contain impurities having boiling points below the boiling point of tertiary butyl alcohol including oxygenated impurities and molybdenum catalysts and an impure propylene oxide feedstock fraction 40 which, in accordance with the present invention, is charged to a solvent extraction zone 50 which may be of any conventional construction, such as a solvent extraction tower as described in Perry's *Chemical Engineer's Handbook*.

In accordance with the present invention, water is charged to the solvent extraction zone 50 by way of a water charge line 52 and a $C_8$-$C_{10}$ paraffinic extractant such as octane is charged to the solvent extraction zone 50 by way of a line 54. Suitably, from about 100 to about 500 parts of water and from about 50 to about 500 parts of paraffinic hydrocarbon are charged to the solvent extraction zone 50 per 100 parts by volume of impure propylene oxide feedstock.

Within the solvent extraction zone 50 a countercurrent solvent extraction occurs resulting in the formation of an overhead supernatent extract phase 56 which is composed of paraffinic solvent and substantially all of the $C_6$ hydrocarbon impurities charged to the solvent extraction zone 50 together in the propylene oxide fraction 40.

A raffinate fraction 58 composed of water and propylene oxide is withdrawn from the extraction zone 50 and charged to a distillation zone 60, which may suitably be a simple distillation zone where it is separated by fractional distillation into a bottom water fraction 62 and an overhead purified propylene oxide fraction 64 that will contain not more than about 50 ppm of $C_6$ hydrocarbon impurities, such as from about 1 to about 50 ppm of $C_6$ hydrocarbon impurities.

Figure 2:
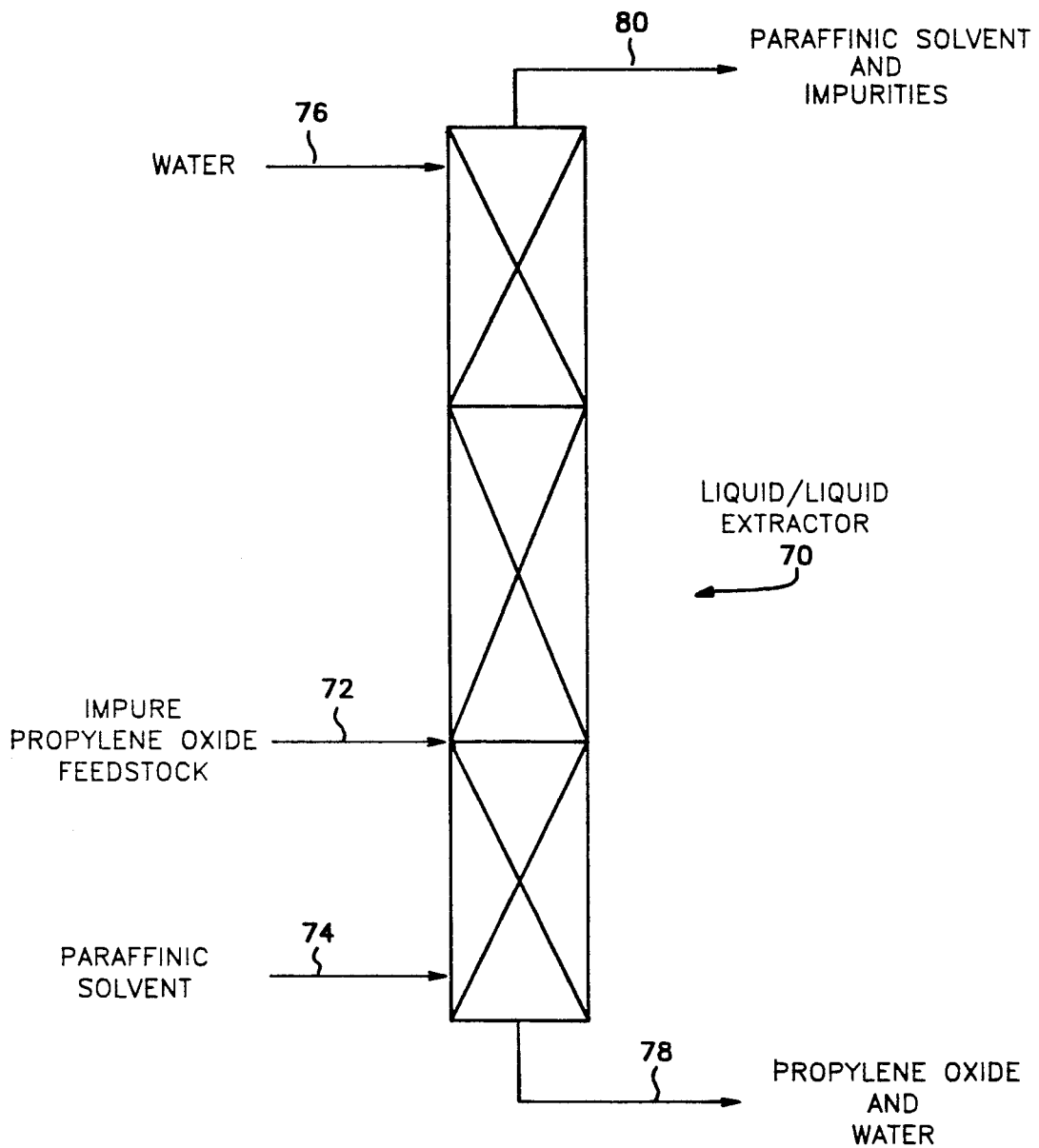
FIG. 2 is a schematic plan view illustrating a preferred method for the continuous practice of the process of the present invention.

Turning now to FIG. 2, there is shown a schematic plan view illustrating a preferred method for the continuous practice of the process of the present invention. In accordance with this embodiment, an impure propylene oxide feedstock is obtained, for example, by the distillation of an epoxidation reaction mixture, as described above, which is contaminated with more than about 50 ppm of $C_6$ hydrocarbon impurities such as hexanes, hexenes, methyl pentenes and methyl pentanes.

The impure propylene oxide feedstock is continuously charged to a liquid-liquid extraction column 30 by a propylene charge line 72, which is preferably located at or below the midpoint of the column. At the same time, a $C_8$-$C_{10}$ paraffin solvent, such as isooctane is continuously charged to the extraction column 70 adjacent the bottom thereof by a charge line 74, and water is continuously charged to the extraction column 70 adjacent the top thereof by a charge line 76. As explained above, from about 100 to about 500 volumes of water and from about 50 to 500 volumes of paraffinic hydrocarbon solvent are charged to the solvent extraction column per 50 to 100 volumes of impure propylene oxide feedstock.

Within the extraction tower 70, the ascending paraffinic solvent will absorb the $C_6$ hydrocarbon impurities and the solution of $C_6$ hydrocarbon impurities in the paraffinic solvent will be continuously discharged from the extraction tower 70 by a discharge line 78. At the same time, the descending water co-solvent will keep the propylene oxide from dissolving in the paraffinic solvent and the propylene oxide and water will be continuously discharged from the extraction tower 70 by a discharge line 80.

Preferably, the impure propylene oxide feedstock charge line 72 is located at least one theoretical stage above the paraffinic charge line 74 and, preferably, the water charge line 76 is located at least two theoretical stages above the charge line 72. It will be understood that additional extraction stages may be added, if desired, above and/or below the charge line 72 in order to improve the efficiency of the extraction.

The solvent extraction tower 70 is preferably operated at ambient conditions of temperature and pressure. When operating at or about atmospheric pressure and at temperatures of less than about 100° F., only a negligible amount of the propylene oxide will react with the water to form propylene glycol. At higher operating temperatures, such as the elevated temperatures normally used in the reboiler for an extractive distillation column, significant undesirable reaction of the propylene oxide will occur.

It will be understood that, if desired, the water and the impure propylene oxide feedstock may be mixed before being charged to the solvent extraction tower 70.

EXAMPLES

The invention will be further illustrated by the following examples which are given by way of illustration and not as limitations on the scope of this invention.

Experiment 6538-9

To 125 ml of propylene oxide containing 857 ppm 2-methyl pentane and 56 ppm 4-methyl-1-pentene, often referred to as "dimer" in the literature, was added 300 ml of deionized water. This mixture was then extracted at room temperature with 125 ml of isooctane in a separatory funnel. Two layers formed upon settling, the upper isooctane layer having a volume of 175 ml and the lower propylene oxide/water layer having a volume of 365 ml. The lower layer analyzed at 1.8 ppm 2-methyl pentane and 1.1 ppm 4-methyl-1-pentene on a pure propylene oxide basis.

The upper layer was extracted at room temperature with 175 ml of deionized water in a separatory funnel and allowed to settle. Two layers formed, the upper isooctane layer having a volume of 145 ml and the lower water/propylene oxide layer having a volume of 200 ml. The lower layer analyzed at 4.0 ppm 2-methyl pentane and 2.5 ppm 4-methyl 1 pentene on a pure propylene oxide basis.

The upper layer was extracted once more at room temperature with 145 ml of deionized water in a separatory funnel and allowed to settle. Two layers formed, the upper isooctane layer having a volume of 130 ml and the lower water/propylene oxide layer having a volume of 155 ml. The upper isooctane layer contained 6.2 wt. % propylene oxide, 652 ppm 2-methyl pentane, and 78 ppm 4-methyl-1-pentene. The lower layer analyzed at 17.1 ppm 2-methyl pentane and 7.2 ppm 4-methyl-1-pentene on a pure propylene oxide basis.

The above experiment demonstrates that it is possible to substantially reduce the concentration of trace hydrocarbons in propylene oxide by extraction with an appropriate hydrocarbon solvent. Water is needed in the extraction process in order to keep the majority of the propylene oxide in a liquid phase separate from the hydrocarbon solvent. Subsequent water washing of the hydrocarbon solvent removes additional propylene oxide so that the losses of propylene oxide to the solvent phase can be minimized.

Having thus described our invention, what is claimed is:

1. In a continuous method wherein propylene is continuously reacted with an organic hydroperoxide in the presence of a soluble molybdenum catalyst to provide an epoxidation reaction product comprising unreacted propylene, propylene oxide, a hydroxy derivative of the organic hydroperoxide, oxygen containing impurities and one or more 6 carbon atoms hydrocarbon impurities selected from the group consisting of hexane, hexene, 2-methyl pentane, 4-methyl pentene-1, 4-methyl pentene-2, and 2-methyl pentene-2, and wherein the epoxidation reaction product is continuously separated in a distillation zone into a plurality of fractions including an impure propylene oxide distillation fraction feedstock contaminated with from about 100 to about 1,000 ppm, based on propylene oxide, of said 6 carbon atom hydrocarbon impurities, the improved method for continuously removing substantially all of said 6 carbon atom hydrocarbon impurities from said impure propylene oxide distillation fraction feedstock which comprises:

continuously charging said impure propylene oxide distillation fraction feedstock to a liquid/liquid extraction column and continuously contacting said impure propylene oxide distillation fraction feedstock therein with an extractant consisting essentially of water and a paraffinic extractant containing 8 to 10 carbon atoms, continuously resolving said impure propylene oxide distillation fraction feedstock and said extractant in said liquid/liquid extraction column into a raffinate consisting essentially of an aqueous solution of propylene oxide containing from about 10 to about 50 ppm, based on the propylene oxide, of the said 6 carbon atom hydrocarbon impurities initially present in said impure propylene oxide distillation fraction feedstock, and continuously charging said raffinate to a distillation zone and continuously separating it therein by simple distillation into a water fraction and a purified propylene oxide product containing from about 10 to about 50 ppm, based on the propylene oxide, of the said 6 carbon atom hydrocarbon impurities initially present in said impure propylene oxide distillation fraction feedstock.

2. A method as in claim 1 wherein the organic hydroperoxide is tertiary butyl hydroperoxide, wherein the epoxidation reaction product comprises propylene, propylene oxide, tertiary butyl alcohol, unreacted tertiary butyl hydroperoxide and said impurities and wherein the epoxidation reaction product is separated in the distillation zone into a propylene fraction, said impure propylene oxide distillation fraction feedstock, and a tertiary butyl alcohol fraction.

3. A method as in claim 2 wherein the paraffinic hydrocarbon extractant is isooctane.

4. A continuous method for the recovery of purified propylene oxide from an impure propylene oxide feedstock contaminated with from about 100 to about 1,000 ppm of one or more 6 carbon hydrocarbon impurities selected from the group consisting of hexane, hexene, 2-methyl pentane, 4-methyl pentene-1, 4-methyl pentene-2, and 2-methyl pentene-2, said method comprising the steps of:

continuously charging said impure propylene oxide feedstock to a liquid/liquid extraction column and continuously countercurrently contacting said impure propylene oxide feedstock therein under ambient conditions of temperature and pressure with an extractant consisting essentially of water and isooctane, the water being continuously charged to said liquid/liquid extraction column at least two theoretical stages above the point of introduction of the impure propylene oxide feedstock, and the isooctane being charged to said liquid/liquid extraction column at least one theoretical stage below the point of introduction of the impure propylene oxide feedstock, the water and isooctane being continuously charged in amounts such that the volume ratio of water to propylene oxide in the impure propylene oxide feedstock is in the range of about 1 to about 5 unit volumes of water per unit volume of propylene oxide and such that the volume ratio of isooctane to propylene oxide feedstock is in the range of about 0.5 to about 5 unit volumes of isooctane per unit volume of propylene oxide feedstock, continuously resolving said impure propylene oxide feedstock and said extractant in said liquid/liquid extraction column into a raffinate consisting essentially of an aqueous solution of propylene oxide containing from about 10 to about 50 ppm, based on the propylene oxide, of said 6 carbon atom hydrocarbon impurities initially present in said propylene oxide feedstock and into an extract fraction comprising said isooctane and a major amount of the 6 carbon atom impurities is initially present in said impure propylene oxide feedstock, and continuously charging said raffinate to a distillation zone and continuously separating it therein by simple distillation into a water fraction and a purified propylene oxide product fraction containing from about 1 to about 50 ppm, based on the propylene oxide, of the said 6 carbon atom hydrocarbon impurities initially present in said propylene oxide feedstock.

* * * * *